United States Patent [19]

Levine et al.

[11] Patent Number: 5,342,790
[45] Date of Patent: Aug. 30, 1994

[54] APPARATUS FOR INDIRECT FLUORESCENT ASSAY OF BLOOD SAMPLES

[75] Inventors: Robert A. Levine, Guilford; Stephen C. Wardlaw, Old Saybrook, both of Conn.; Leon W. M. M. Terstappen, Palo Alto, Calif.; Thomas J. Mercolino, Stockton, N.J.; Diether J. Recktenwald, Cupertino, Calif.

[73] Assignee: Becton Dickinson and Company, Franklin Lakes, N.J.

[21] Appl. No.: 969,379

[22] Filed: Oct. 30, 1992

[51] Int. Cl.$^5$ .......................................... G01N 33/536
[52] U.S. Cl. ........................ 436/523; 422/58; 422/72; 422/101; 435/296; 436/164; 436/165; 436/514; 436/518; 436/528; 436/531; 436/534; 436/536; 436/538; 436/541; 436/805; 436/810; 436/824; 436/829
[58] Field of Search ................ 422/57, 58, 72, 73, 422/101; 435/296, 971; 436/45, 70, 164, 165, 514, 518, 523, 528, 531, 534, 536, 538, 541, 805, 810, 824, 829

[56] References Cited

U.S. PATENT DOCUMENTS

| | | | |
|---|---|---|---|
| 4,190,328 | 2/1980 | Levine et al. | 356/246 |
| 4,378,344 | 3/1983 | Zahradnik et al. | 436/810 |
| 4,480,038 | 10/1984 | Cheng | 435/29 |
| 4,721,681 | 1/1988 | Lentrichia et al. | 436/523 |
| 4,940,668 | 7/1990 | Wardlaw et al. | 436/17 |

OTHER PUBLICATIONS

Pharmacia LKB Biotechnology Products, 1988.

Primary Examiner—Toni R. Scheiner
Assistant Examiner—Christopher L. Chin
Attorney, Agent, or Firm—William W. Jones

[57] ABSTRACT

A patient's health is diagnosed by centrifuging blood samples in a transparent tube, which tube contains one or more groups of particles such as lyposomes or plastic beads of different densities for each group. Each group of density-defined particles carries antigens or antibodies which are specific to a complement antigen or antibody which may be in the blood sample being tested, and which are indicative of the patient's health. A label-tagged antibody which is specific to all bound antibody/antigen couples is added to the blood sample so as to form labeled antibody+antigen-antibody complexes (AAAC) in the blood sample. Upon centrifugation, the complexed particles will settle out in different areas in the tube according to the respective density of the particles, and the degree of label emission of the particle layers can enable qualitative or quantitative analyses of the blood sample to be made. Unbound labeled antibodies will be washed away from the complexed layers by the washing action of the descending blood cells during the centrifugation step. Unbound labeled antibodies will thus not interfere with the analysis.

7 Claims, 1 Drawing Sheet

APPARATUS FOR INDIRECT FLUORESCENT ASSAY OF BLOOD SAMPLES

TECHNICAL FIELD

This invention relates to the one-step simultaneous determination of the presence or absence of either partner component of one or more active couples of binding biologic particles, and where desired, their quantification in a whole blood, blood plasma, or serum sample.

BACKGROUND ART

Analyses of blood samples for the presence or absence of antibodies or antigens are used in the diagnosis of diseases, such as HIV infection, hepatitis, Lyme disease, prenatal profiles including TORCH (an acronym for: "Toxoplasmosis, Rubella, Cytomegalovirus, Herpes") profiles, as well as other infectious disease profiles. Presently, such serologic diagnoses are often performed by standard indirect fluorescent immunoassay. In a standard indirect fluorescent immunoassay, an antigen, which is the coupling partner for the antibody to be detected, is first affixed to a solid support medium such as a glass slide, a paper membrane or the like. A sample of serum from the patient is then allowed to incubate in contact with the affixed antigen for a period of time sufficient for the partner antibody, if present, to become attached to the affixed antigen. The support surface is then washed to remove all unbound antibodies. A reagent consisting of a labelled antibody to human immune (antibody) globulins is next brought into contact with the support surface and incubated for a time sufficient to cause linkage of the labelled material and any traces of the patient's antibodies which may have bound to the fixed antigen. The excess reagent is then washed off and the support surface is examined to determine if any label is present. Examination of the prepared sample is done visually, or by by spectrophotometry or fluorometry. It will be appreciated that the aforesaid procedure requires multiple specimen handling steps, including washing, and analysis techniques, and is thus labor intensive and time-consuming. The aforesaid procedure can detect the presence or absence of only one antigen-specific antibody per test, but cannot differentiate between specific IgG or IgM without further testing, nor can it detect multiple antigens and/or antibodies simultaneously.

DISCLOSURE OF THE INVENTION

Copending U.S. Ser. No. 07/770,875, filed Oct. 4, 1991, discloses a method and paraphernalia for performing differential erythrocyte counts by forming densimetrically distributed bands of microbeads having different band specific gravities, hereinafter referred to as density-markers. This invention relates to a method and paraphernalia for rapidly and easily determining the presence or absence of either partner component of one or more active couples of binding biologic particles in whole blood, sera or plasma samples. Examples of such detectable couples are: TSH/Anti TSH complex; T4/Anti T4 complex; Rubella antibody/Anti Rubella antibody; HIV antibody/HIV antigen; all of which are where the TSH, the T4, the Rubella antibody, and the HIV antibody are the target analytes. The method is performed in a centrifuge tube by merely centrifuging the blood sample containing the several reagents in the tube, and observing the results of the centrifugation step. The determination can be made without exposing the physician or technician to the blood sample.

Red cells, when centrifuged in a tube containing a whole blood sample will form a continual density gradient layer in the bottom of the tube, with the most dense red cells settling on the bottom of the red cell layer. When the blood sample is centrifuged in a tube containing the groups of different specific gravity micro bead density-markers referred to above, or different specific gravity lipsome density-marker, the microbeads or lipsomedensity-markers will form spaced, distinctly visible marker rings in the packed red cell layer. The centrifuge tube may also contain a cylindrical plastic insert which may be fixed to the bottom of the tube or may be freely movable in the tube, and which, if freely movable, has a specific gravity such that it will sink through the red cell layer in the centrifuged blood sample. The insert restricts the available space in the tube which the red cells can occupy, and therefore increases the distance between the marker rings which form in the centrifuged red cell layer, and displaces the microbead or lipsome density-markers to the periphery of the tube where they may be seen and easily detected without their signal being extinguished by the red cells.

In performing the method of this invention, the microbead or lipsome density-marker will be coupled with an antigen or antibody, or another biologically active substance whose complement, or binding partners, (which may be designated as "the target analytes") may be present in the patient's blood. Examples of biologically active complementary couples include: enzymes and their substrates; nucleotides and their complementary nucleotides; naturally occurring protein binders, such as thyroid binding globulin (TGB) and thyroxine; the "intrinsic factor", and vitamin B-12; and specific antibodies which will selectively couple with RNA-DNA hybrids, as described by Stollar and Rashtchian, in their article "Immunochemical Approaches to Gene Probe Assays", *Analytical Biochemistry* 1987; 161, 387–394.

Each density-marker group, of which there may be only one, will be bound with a coupling particle, which is specific to a target analyte, which analyte may be present in the blood or other biological specimen sample. The sample is added to the tube so as to allow the density-marker/coupling particle group or groups to intermix with the sample sufficiently to cause any target analytes present in the sample to couple with their complement partners on the density-markers.

When bound couples are created using the method of this invention, after the coupling step is completed, a labeled or tagged "anti-antigen-antibody-complex" antibody (AAAC antibody) which is specific to (and which may be in the tube prior to addition of the sample thereto) all couples on the density-markers will bind to any of the density-markers which have target analyte/coupling particle couples thereon. This AAAC antibody may be dry coated on the interior of the tube, for example, or may be present in liquid form in an evacuated tube such as described in U.S. Pat. No. 5,086,784, granted Feb. 11, 1992 to Robert A. Levine and Stephen C. Wardlaw.

AAAC antibodies of this type have been made by the Immunocytometry System Division of Becton Dickinson and Company, of San Jose, Calif. Instead of being specific to all antigen/antibody couples, the tagged AAAC antibody may be specific for immune globulin subgroups (IgG or IgM antibody-antigen complexes). Likewise, if the desired analyte is an RNA or DNA, then the tube will contain a labeled antibody that is specific to or will bind to the RNA-DNA pair, as described in Stollar and Rashtchian.

The label may be a liposome encapsulated colorant, or a fluorescent colorant; or may be a radioactive energy emitter. The label must be detectable and preferably quantifiable. The tagged AAAC antibody binds to all of the density-markers which have couples formed thereon. The sample is centrifuged to densimetrically separate the density-markers into spaced-apart bands or rings in the tube. The different density-marker bands are then examined in the tube to determine which bands, if any, have a detectable quantity of the label, and to measure the quantity of the label, if appropriate. The label most likely to be used would be a fluorescent molecule such as FITC.

If desired, the different density-markers can have different intrinsic colors, so that each (if there are more than one band) differently colored band will designate a different target analyte. If differently colored density-markers are used, the colors of the labeled bands in the tube will indicate which bound analytes are in the sample, and which analytes are not, in the event that bands of density-markers placed in the tube do not demonstrate any label associated therewith. If colored density-markers are not used, then the position of the labeled bands in the tube will indicate which analytes are in the sample, and which are not. This information, of course, permits diagnosis of the health of the sample donor.

It is therefore an object of this invention to provide an improved technique for analyzing a biological specimen sample to determine the presence or absence of certain target analytes therein.

It is a further object to provide an improved technique of the character described wherein the analysis is performed densimetrically in a transparent specimen tube.

It is an additional object of this invention to provide an improved technique of the character described wherein the analysis is performed by using density-markers of different specific gravities coupled to antibodies and/or antigens so that multiple assays may be performed in one tube at one time.

It is another object of this invention to provide an improved technique of the character described wherein the analysis is performed by forming highlighted antibody/antigen couple bands in the sample.

These and other objects and advantages will become more readily apparent from the following detailed description of a preferred embodiment of the invention when taken in conjunction with the accompanying drawing in which:

DETAILED DESCRIPTION OF THE BEST MODE

Figure 1:
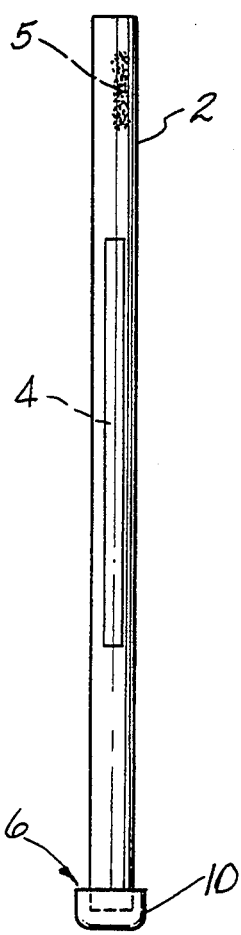
FIG. 1 is side elevational view of a centrifuge tube adapted to perform the procedure of this invention.
Figure 2:
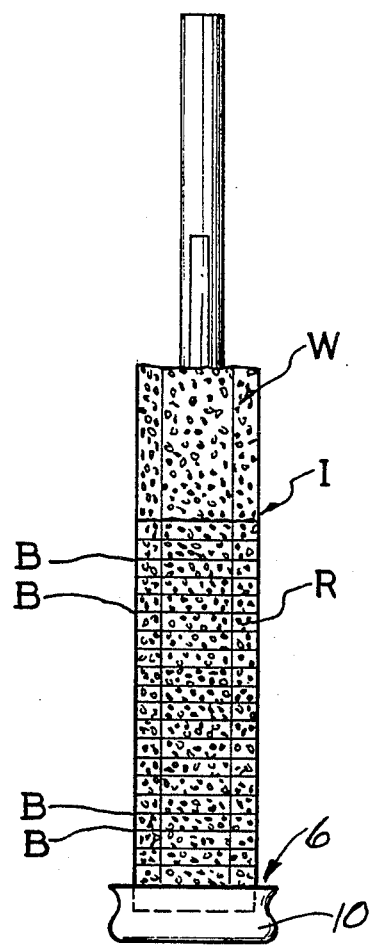
FIG. 2 is a view of the tube of FIG. 1 showing a centrifuged whole blood sample therein, and with the red blood cell layer being blown up or increased in size to particularly point out the nature of the invention.

Referring now to FIGS. 1 and 2, there is shown in FIG. 1, a tube 2, which may be a glass capillary tube, or other transparent tube, and which may contain a float or insert 4 made of a plastic, which has a specific gravity that causes the insert 4 to settle through the red blood cells to the bottom 6 of the tube 2 when the latter is centrifuged with the blood sample therein. The fraternal groups of antibody and/or antigen-coupled density-markers of different specific gravities may be disposed in a clump 5 in the tube 2. A plastic cap 10 closes the bottom 6 of the tube 2. The specific gravity of each group of density-marker will be greater than the specific gravity of the lightest of the red cells, i.e., the youngest reticulocytes.

The blood sample is drawn into the tube 2 and, after a suitable incubation period, is centrifuged therein along with the insert 4 and density-marker 5. The density-marker clump 5 disperses in the blood sample during the incubation period, and then settles into distinct bands which form lines in the red cell layer as shown in FIG. 2 during the centrifugation step, while the float 4 settles into and through the red cells R. The tube 2 will also contain the tagged AAAC antibodies described above.

The white cells W layer out in bands above a red cell/white cell interface I. The density-marker density-marker bands B layer out densimetrically in the the red cell layer. Examination of the bands B will indicate which of the bands B have been tagged since the fluorophore tags will be detectable only in tagged bands.

Figure 3:
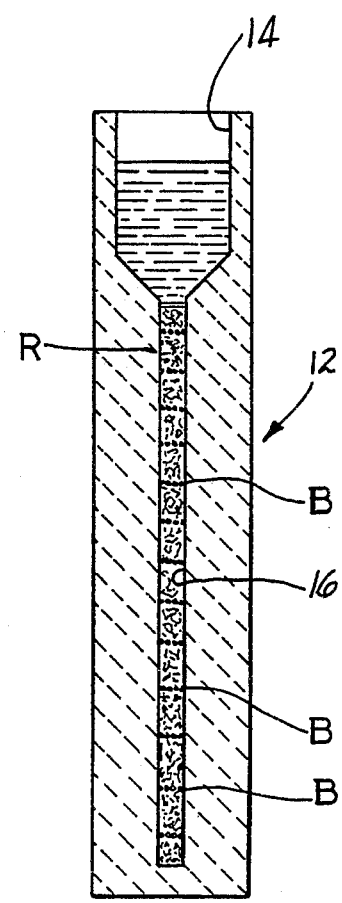
FIG. 3 is an axial sectional view of a second embodiment of a centrifuge tube adapted for use in performing the invention.

FIG. 3 shows an alternative form of centrifuge tube which can be used to practice the invention. The tube 12 has a compound funnel-shaped bore with an enlarged open end part 14 and a restricted closed end part 16. The bore is sized so as to cause the red cells R in the centrifuged blood sample to settle into the restricted part 16 of the bore, with the white cells and plasma staying for the most part in the enlarged part 14 of the bore. The tagged density-marker bands B disperse in the centrifuged red cell layer. The tube 12 is formed from a transparent glass or plastic material. It will be noted that the embodiment shown in FIG. 3 does not use a float component.

It will be noted from FIGS. 2 and 3 that the density-marker bands are sufficiently spaced apart that each can be assayed for fluorescence, or other energy emissions, and can even be quantified as set forth hereinafter, without interference from any other bands B. When a blood sample is assayed, the nature of the red blood cells, i.e., the fact that they pack when centrifuged in a manner which excludes the plasma, ensures that virtually all of the non-bound labeled AAAC antibodies in the tube will end up in the plasma layer, and will not interfere with the procedure.

A general example of the use of the invention to quantify a target analyte in a sample is as follows. The physician will identify from the literature an approximate range of how many molecules or units of a target analyte can be expected to be found in a known volume sample of the biologic fluid being assayed. For example, assume that a patient infected or exposed to Lyme Disease will be expected to have 50 Lyme analyte units per millileter of blood at the most. The physician will add at least 100 density-marker/antigen/antibody coupled units to the blood sample per millileter being sampled, and will also add at least 100 labelled AAAC antibodies per millileter of sample to the container. Since there are an excess of bonding sites and tagging particles in the sample as compared to the maximum number of analyte units expected to be found in the sample, the degree or intensity of label emission from the Lyme bead band will be proportional to the number of Lyme analytes which are actually present in the sample. A quantification of the Lyme analyte in the blood can thus be approximated by measuring the emission intensity. The key to the quantification procedure is to provide a functional excess of binding sites and tagged antibodies in the sample as compared to the maximum number of analyte units which can be expected to be found in the sample. One may still be able to quantitate the analyte even if the bonded-AAAC antibody units are present in molar amounts less than the analyte, provided that there exists a mathematical relationship between the amount of analyte present and the amount of analyte eventually bound to the density marker-AAAC antibody couples.

In cases where a laboratory wishes to utilize serum or plasma samples, or where more predictable density gradients are required, such as might be the case if many densities need to be separated, then the narrowed portion of the tube shown in FIG. 3 could be prefilled with a stable material, such as gelled Ficoll, having the required density gradient. This density gradient material, in addition to separating the resident bands, will serve to wash the unbound AAAC antibodies away from the bound layers during the centrifugation step.

It will be appreciated that the invention has been described in connection with blood diagnosis, but the invention is also applicable to diagnose other biological fluids for the presence or absence of highly specific complement couples found in such other biological fluids. As with the analysis of plasma, when a biological fluid other than whole blood is assayed, the centrifugation step should be performed in the density gradient fluid, such as Ficoll gel, as noted above, which will not mix with the aqueous phase of the biological fluid, and will allow densimetric separation of the bands in the density gradient fluid, with concurrent washing by the gradient fluid of the density-markers, to ensure separation of all non-bound label from the bands. This eliminates non-bound label interference with quantification of the labeled bands. The inherent washing of non-bound label from labeled cells when whole blood is being tested, and when a non-cellular fluid is being tested in gelled Ficoll, which washing occurs during the centrifugation step, eliminates the separate washing steps required by the prior art, and prevents unbound label from interfering with the accuracy of the procedure. This inherent washing is an important contributor to the operability of this invention.

Since many changes and variations of the disclosed embodiments of the invention may be made without departing from the inventive concept, it is not intended to limit the invention otherwise than as required by the appended claims.

What is claimed is:

1. Paraphernalia for use in centrifugally analyzing a biological fluid sample for the presence or absence of a target analyte, said paraphernalia comprising:
   a) a transparent tube having a bore for receiving the fluid sample;
   b) means for forming a local constriction in said tube bore;
   c) a quantity of target analyte-specific antibody and/or antigen-coupled density-markers in said tube; and
   d) means for forming a density gradient layer in said tube into which the density markers sink during centrifugation of the sample in said tube.

2. The paraphernalia of claim 1 wherein said density-marker include several different groups of beads or liposomes, each group having a specific gravity that is different from the specific gravity of the beads or liposomes in each of the other groups.

3. The paraphernalia of claim 1 wherein the sample to be tested is whole blood containing red blood cells, and said density-markers have a specific gravity which is greater than the specific gravity of the lightest of the red blood cells in the sample of whole blood.

4. The paraphernalia of claim 1 further comprising labeled anti-antigen-antibody-complex (AAAC) antibodies in said tube, said AAAC antibodies being specific to any antibody/antigen/analyte couples formed on said density-markers and being operable to detectable highlight said couples.

5. The paraphernalia of claim 4 wherein the antibody and/or antigen-coupled density markers and labeled AAAC antibodies are present in the tube in an amount which exceeds the amount of target analyte units expected to be found in the sample to an extent sufficient to quantify the target analyte in the sample.

6. The paraphernalia of claim 5 wherein the amount of antibody and/or antigen-coupled density-markers and labeled AAAC antibodies is at least twice the expected quantity of the target analyte.

7. Paraphernalia for use in centrifugally analyzing a biological fluid sample for the presence or absence of immune globulin subgroups, said paraphernalia comprising:
   a) a transparent tube having a bore for receiving the fluid sample;
   b) means for forming a local constriction in said tube bore;
   c) a quantity of immune globulin-specific antibody and/or antigen-coupled density-markers in said tube;
   d) an operable amount of labeled anti-antigen-antibody-complex (AAAC) antibodies in said tube, said AAAC antibodies being specific to immune globulin antibody-antigen complexes formed on said density-markers and being operable to detectably highlight said complexes; and
   e) means for forming a density gradient layer in said tube into which said density-markers will sink during centrifugation.

* * * * *